(12) United States Patent
Sarma et al.

(10) Patent No.: US 7,288,376 B2
(45) Date of Patent: Oct. 30, 2007

(54) METHOD OF DETECTION OF SP-A2 GENE VARIANTS USEFUL FOR PREDICTION OF PREDISPOSITION TO ASPERGILLOSIS

(75) Inventors: Puranam Usha Sarma, Delhi (IN); Taruna Madan, Delhi (IN); Shweta Saxena, Delhi (IN)

(73) Assignee: Council of Scientific and Industrial Research, New Delhi (IN)

( * ) Notice: Subject to any disclaimer, the term of this patent is extended or adjusted under 35 U.S.C. 154(b) by 481 days.

(21) Appl. No.: 10/686,786

(22) Filed: Oct. 17, 2003

(65) Prior Publication Data

US 2004/0137476 A1 Jul. 15, 2004

Related U.S. Application Data

(63) Continuation-in-part of application No. 10/102,731, filed on Mar. 22, 2002, now abandoned.

(51) Int. Cl.
*C12Q 1/68* (2006.01)
*C12P 19/34* (2006.01)
*C07H 21/04* (2006.01)

(52) U.S. Cl. .................. 435/6; 435/91.2; 536/24.33

(58) Field of Classification Search ............... 435/91.2, 435/6
See application file for complete search history.

(56) References Cited

OTHER PUBLICATIONS

Madan et al. (2002) Association of polymorphisms in the collagen region of human SP-A1 and SP-A2 genes with pulmonary tuberculosis in Indian population. Clin. Chem. Lab Med. 40(10): 1002-1008.*

"Characterization of a Second Human Pulmonary Surfactant-Associated Protein SP-A Gene", Kikandar L. Katyal, et al., Am., J. Respir. Cell Mol. Biol., vol. 6, pp. 446-452, 1992.

"Isolation and Characterization of the Human Pulmonary Surfactant Apoprotein Gene", L. Tyler White, et al., Nature, vol. 319, pp. 361-363, 1985.

"Association of Polymorphisms in the Collagen Region of *SP-A2* with Increased Levels of Total IgE Antibodies and Eosinophilia in Patients with Allergic Bronchopulmonary Aspergillosis", Shweta Saxena, et al., J. Allergy Clin. Immunol., vol. 11(5) 1001-1007 (May 2003).

NCBI Sequence Viewer for GenBank Accession No. M30868, (May 1994).

Sequence Revision History for M30868, M30838 and M68519, (1994).

NCBI Sequence Viewer for GenBank Accession No. M68519, (1995).

Kavanagh et al., Br. J. Biomed. Sci (2001) 58: 197-205.

Madan et al., J. Allergy Clin. Immun. (2000) vol. 105, No. 1 part 2, p. S301.

Priyanka et al., J. Allergy Clin. Immun. (1998) vol. 101, No. 1 part 2, p. S78.

Madan et al., J. Clin Invest (2001) 107(4): 467-475.

* cited by examiner

*Primary Examiner*—Jeffrey Fredman
*Assistant Examiner*—Angela Bertagna
(74) *Attorney, Agent, or Firm*—Smith, Gambrell & Russell, LLP

(57) ABSTRACT

Allele specific primers and probes suitable for detecting allelic variants of human SP-A2 gene for applications such as molecular diagnosis, prediction of an individual's susceptibility, and/or the genetic analysis of SP-A2 gene in a population.

4 Claims, 2 Drawing Sheets

SP-A2 GENE (M68519)

SNPs at 1649 position (91st codon),
1660 position (94th codon)

SEQUENCE LISTING

<160> NUMBER OF SEQ ID NOS: 1

<210> SEQ ID NO 1
<211> LENGTH: 4731
<212> TYPE: DNA
<213> ORGANISM: Homo sapiens

<400> SEQUENCE: 1

```
tccagcctga gtgttctgca gggaaatgtg ctgtgtaaac actatgccta tttcctgctt      60
ggagaacagg ttttgaggta gagctctcag gggtggggaa gaagcctggc agcccacatg     120
ctataaatgc tgttgtccac ctttatgctc taacttggag gcagagaccc aagcagctgg     180
aggctctgtg tgtgggtgag tttagccaca tcccctaggt gttctccagc ttgaggatcg     240
caggcagaga ggaccagccc agcagccaca ggcctgacca aggccaggtt gggaaggagg     300
gcaactcccc attttccact gggaggtgtt tcacagcatg gtcaacatgg atgacctaca     360
aagaccctca tgctttgata tcttccttgg ccagatccat ccctaccagg gactcagcag     420
ggcctaagca gggggagtgg gagaacagac cccaagagga aggaagacct catcactgac     480
tgtgagaggg tcatcacccc ccgatgatca ccttgaaggg tccaggctgt gggccctatt     540
catctctttt cattctcagg tcgctgattt cttggagcct gaaaagaagg taactgggca     600
atgagggaca gatggagtga gtcagtgagt gagtgaccte atccttcctc ctaacagcct     660
gggagggaca gggcaggttt tctgcagagc atggaagatt cagctgaaat cagagaggtg     720
aagccagttt cccagggtaa catagtgagg cactgaaaga aaggagactg cactgagccc     780
aggtccctgg gctccccaga gctccttact cttcctcctc ctcagcagcc ttgagacccc     840
acaacctcca gccggaggcc tgaagcatga ggccatgcca ggtgccagat gatgcttgga     900 atttteccegg gtgcttcggg tcttcccagc actctggtct cgcccgccct gcctctcgct     960
ctgcccagct tcctgagtcc tgacagagca cagtggggga agatgttggc agaggtggca    1020
gatgggctca cggccatccc tccagcagga gcagcgactg gacccagagc catgtggctg    1080
tgccctctgg ccctcaacct catcttgatg gcagcctctg gtgctgcgtg cgaagtgaag    1140
gacgtttgtg ttgaagccc tggtatcccc ggcactcctg gatcccacgg cctgccaggc    1200
agggacggga gagatggtgt caaaggagac cctggccctc caggtactgt gctgcagacc    1260
ccaccctcag ctgagggaca cagacccctt ttcaggaggc ccatctgtcc aggcccctag    1320
gctgtgggcc atagtgagct gggggctata gtaagctggg tgggacttca gtctgcaggg    1380
ctggtgggtt cctggggccc ttatgatggc gcatcctgga gagtctgtcc tcatagtgcc    1440
cacggagtga tagctgagcc agccccggtg ataatgggca tcgagtctca ttagctccaa    1500
ccagttgtgg gtgacagatc ctacacatcc atgtctcttt tctctgcagg ccccatgggt    1560
ccgcctggag aaacaccatg tcctcctggg aataatgggc tgcctggagc ccctggtgtc    1620
cctggagagc gtggagagaa gggggaggct ggcgagagag gccctccagg tgagcagggc    1680
```

-continued

```
gggcaggtgg gcagtggaaa catgggcaca gcgacctgaa gtcagttaca cagggggtgat   1740
gggggtcaga caaaccctgc aggtacccca agggcatttg gctcaaccta agtaagagaa   1800
tatgaatttg agggagaaag ccgaggtgtc tggggagtgt ggtcacaatt cagagaaggg   1860
caggtgtggg aagtcctccg tgcctcatga ccgctgatgg ggacacactg agtcaggtgt   1920
gggacgaggg acagctctgg gaggcagggg aggcatgtcc tgggatggag ccctgggggc   1980
agtctgaagg gtgaatgcgg acgaggcatc caggcagatg gtgtgatcag gagccccaca   2040
gacagagggg aactttgaag ctcagagcgg taagcaagtc catcagggca gtgcagagag   2100
catcatgctt gcccttggtg gagggtgcgg gagagggact tgccccacag aggcgggcag   2160
acagaaccc tcgagggaca gagcaggaaa gaggacaagg ggtgggggtc tcagcagggg    2220
caaggcttca ctaaagaata ggggaccacg gggtgtggag acacactgga atctcgtgga   2280
ccctctgagc ctagggtctg ggtggtgcct aacagcaatg aaagggcaga gttccaggat   2340
tgcagatggc aaaacgcctg cgtggcagca agtgggagtc ttcactggcc tgcccctcct   2400
tctgtgtggg gcactctcca cagggcttcc agctcatcta gatgaggagc tccaagccac   2460
actccacgac ttcagacatc aaatcctgca gacaagggga ggtaagggga cccctgggc    2520
ctcacggggt aggagtttcc cacaaattcc cctcattctc agcaccacct tctagaatag   2580
agatgacaaa caagcgtgca catgcaggtg ttggggaaag gaatgatgct tgctttctg    2640
atgtctttga atggccaaga ggagacaagc agacacaatt cactccccat ttcataagaa   2700
agcaagttct ctgcctgtct tgcttccac tgaatcctag gaaattgcac catttctggc    2760
aataagtaat tgttacttag atgaatgaat aaatggagga gagtctaaaa gtgaatttag   2820
aaaactgcaa ttggaagagg aagagaagac acagagagag cagagatgg agagactggg    2880
gaggatctgg tagcagagac cctaggtgag ggaggtggct tagagacaaa gtggtcagtg   2940
gcctgacctg gactcctctg ctctcagccc tcagtctgca gggctccata atgacagtag   3000
gagagaaggt cttctccagc aatgggcagt ccatcacttt tgatgccatt caggaggcat   3060
gtgccagagc aggcggccgc attgctgtcc caaggaatcc agaggaaaat gaggccattg   3120
caagcttcgt gaagaagtac aacacatatg cctatgtagg cctgactgag ggtcccagcc   3180
ctggagactt ccgctactca gatgggaccc tgtaaactac caccaactgg taccgagggg   3240
agcctgcagg tcggggaaaa gagcagtgtg tggagatgta cacagatggg cagtggaatg   3300
acaggaactg cctgtactcc cgactgacca tctgtgattt ctgagaggca tttaggccat   3360
gggacaggga ggatcctgtc tggccttcag tttccatccc caggatccac ttggtctgtg   3420
agatgctaga actcccttc aacagaattc acttgtggct attagagctg gaggcaccct    3480
tagccacttc attcccctga tgggccctga ctcttcccca taatcactga ccagccttga   3540
cactcccctt gcaaaccatc ccagcactgc accccaggca gccactccta gccttggcct   3600
ttggcatgag atggaggctt ccttattccc catctggtcc agttccttca cttacagatg   3660
gcagcagtga ggccttgggg tagaaggatc ctccaaagtc acacagagtg cctgcctcct   3720
ggtcccctca gctctgcctc tgcagcccac tgcctgccca gagccatcag gatgagcagt   3780
accggccaag cataatgaca gagagaggca gatttcaggg aagccctgac tgtgtggagc   3840
taaggacaca gtggagattc tctggcactc tgaggtctct gtggcaggcc tggtcaggct   3900
ctccaggtgg tcagggcc cagtggtgcc ccagcacggt ggtgcccaag ccaaccctgt     3960
gactgacatg tacgattcac tcctttgagt ctttggatgc caactcagcc ccctgaccctg   4020
```

-continued

```
gaggcagccg gccaaggcct ctagggaaga gcccccact gcagacatga cccgagtaac      4080
tttctgctga tgaacaaatc tgcaccccac ttcagacctc ggtgggcatt cacaccaccc      4140
cccatgccac cggctccact ttcccctttt attaatacat tcacccagat aatcattaaa      4200
attaacatgt gccaggtctt aggatgtgtc ttggggtggg cacagtaccc ggtgactctt      4260
ggggatattt atttattttc cctgagccta tatcttcatc tgtgaaatgg ggataaaaat      4320
acttgttgct gtcacaatta ttaccatctc tccagctagc aaaattacta ccagagccgt      4380
tactacacac aaaggctatt gaccgagcac ataccatgtg ccacacacct tgacaaaatc      4440
ttttaataca gtttattatg tactattcaa tctttacaca atgtcacggg accagtattg      4500
tttacccaat tttttataag gacactgaag cttagaggag tgaaatgttt tgagtgttat      4560
ttcagagagc aaatggcaaa gactggatcc aaacccatct tcctggacct gaagttcatg      4620
ctcccagcca ccccaccct gagctgaata aagatgattt aagcataata aatcgttagt      4680
gtgttcacat gagtttccat agctttggtt ccaagaaaca tcacatttct g              4731
```

METHOD OF DETECTION OF SP-A2 GENE VARIANTS USEFUL FOR PREDICTION OF PREDISPOSITION TO ASPERGILLOSIS

CROSS-REFERENCE TO RELATED APPLICATION

This application is a continuation-in-part of U.S. application Ser. No. 10/102,731, filed Mar. 22, 2002, now abandoned and which is incorporated herein in its entirety by reference.

FIELD OF THE INVENTION

The present invention relates to a method of detection of SP-A2 gene variants useful for prediction of predisposition to aspergillosis. The utility of the invention is in applications such as molecular diagnosis, prediction of an individual's disease susceptibility and genetic analysis of SP-A2 gene in a population. The invention also provides primer sequences useful in detecting these polymorphic variations in SP-A2 gene and their use in diagnosis and prediction of an individual's susceptibility to Allergic bronchopulmonary aspergillosis (ABPA).

BACKGROUND OF THE INVENTION

About the Disease

Aspergillosis is a group of fungal diseases which include allergic bronchopulmonary aspergillosis (ABPA), aspergilloma, chronic necrotising aspergillosis, hypersensitivity pneumonitis and invasive aspergillosis. *Aspergillus fumigatus*, along with other less frequently reported species of *Aspergillus* such as *A. flavus* and *A. niger*, is the major causative fungus. Majority of the fungal allergies are due to *Aspergillus* species, with spores (conidia) and mycelia of the fungus as the infectious forms. *A. fumigatus* is an ubiquitous microbe and universal in distribution. *Aspergillus* species grow at temperatures of 15 to 53° C. in contrast to many fungi that do not grow above 35° C. Two major *A. fumigatus* induced diseases are an allergic form, Allergic bronchopulmonary aspergillosis (ABPA) and an invasive form, Invasive pulmonary aspergillosis. Pulmonary aspergillosis is a serious threat to those immunocompromised as a result of disease or therapy, and has been identified as a major cause of morbidity and mortality in asthmatic and cystic fibrosis patients. Ref: Pulmonary aspergillosis: clinical presentation, diagnosis and therapy. Daly P, Kavanagh K. Br J Biomed Sci 2001;58(3):197-205.

Allergic Bronchopulmonary Aspergillosis (ABPA)

The allergic form of the *Aspergillus* induced disease is named as Allergic bronchopulmonary aspergillosis (ABPA), which is an immunological disease and depicts the immune mechanisms similar to that of asthma. ABPA is often encountered in patients of bronchial asthma (15%, 16 out of 107), cystic fibrosis (7.8%, 191 out of 12,447), sinusitis (13%, 3 out of 23), rhinitis (5%, 3 out of 62). [Chetty et al, 1985; Mastella et al, 2000; Panchal et al, 1997; Grammer et al, 1986]. A study with 35 patients of ABPA showed that 12 (33%) of them were misdiagnosed as patients of pulmonary tuberculosis and were treated with various antitubercular drugs [Behera et al, 1994]. A conglomeration of intertwined *Aspergillus* hyphae matted together with fibrin, mucus and cellular debris, within a pulmonary cavity or ectatic bronchus, is termed as Aspergilloma. Patients of aspergilloma usually have an underlying pulmonary disease such as fibrocystic sarcoidosis, cavitary tuberculosis or histoplasmosis, bullous emphysema, or fibrotic lung disease.

Reference is made to S. Saxena et al., "Association of Polymorphisms in the Collagen Region of SP-A2 with increased levels of total IgE antibodies and Eosinophilia in Patients with Allergic Bronchopulmonary Aspergillosis", *J. Allergy Clin. Immunol.*, Vol. 11(5) 1001-1007 (May 2003).

Diagnosis

Aspergillosis of the lung does not show characteristic clinico-radiological features to permit the diagnosis and should be considered in the differential diagnosis of tuberculosis, pneumonia, bronchiectasis, lung abscess and bronchial asthma. Early diagnosis of ABPA is important for the following reasons: firstly, to prevent irreversible damage of the bronchi and the lungs. Bronchiectasis and bronchiolitis are known sequelae of the disease and if undiagnosed in early stages, may lead to pulmonary fibrosis and respiratory failure. ABPA may be the cause of recurrent pneumonias in children and may increase the severity of asthma in some patients [Chetty et al, 1985]. Association of ABPA in cystic fibrosis may worsen the course and prognosis [Mastella et al, 2000]. ABPA has also been found in multiple members of a family and a need has been felt for screening all the family members of a newly diagnosed case. Occurrence of ABPA is also known to be associated with pulmonary tuberculosis. It has been observed that both diseases show similar clinical symptoms that cause a diagnostic dilemma.

Disease Loci Identified Until Now and Their Associations

Infectious conidia of *Aspergillus fumigatus* are prevalent in the air and the population is exposed to them. However, occurrence of ABPA is limited to individuals with asthma, cystic fibrosis, atopic and other immunocompetent individuals. ABPA is a disease with immunological complexity. Genotype analysis of the T-cell clones (specific for the Asp f 1 antigen), isolated from ABPA patients, showed that most of them are restricted by HLA-DR molecules (90% of the ABPA patients showing a phenotype either HLA-DR2, HLA-DR5 or both) [Knutsen et al, 1994; Chauhan et al, 1994; Chauhan et al, 1996; Chauhan et al, 1997]. HLA-DR molecules DR2, DR5, and possibly DR4 or DR7 contribute to susceptibility while HLA-DQ2 contributes to resistance. Further, a combination of these genetic elements may determine the outcome of ABPA in patients with cystic fibrosis and asthma. Detailed genotype analysis of ABPA patients revealed that susceptibility to ABPA is also associated with alleles of HLA-DR2 and HLA-DR5. The presence of DR4 or DR7 alleles in non-DR2/5 patients with ABPA suggested that these alleles may be contributing factors to pathogenesis. Chauhan et al, 2000, reported a significantly high frequency of HLA-DQ2 in patients without ABPA (67.4%), compared with patients with ABPA (20.5%) and normal control subjects (37.7%), suggesting that these alleles may confer protection in the population without ABPA.

Mutations in cystic fibrosis transmembrane protein (CFTR) encoding gene of cystic fibrosis patients lead to defective synthesis and regulation of cystic fibrosis transmembrane protein. This protein is directly involved in the transportation of chloride ions. Such a defect in chloride transportation results in thick mucus secretion in these patients facilitating colonisation of pulmonary tract by other microbes. Presence of mutations in CFTR gene in ABPA patients suggest that there is some association of ABPA with cystic fibrosis [Miller et al, 1996]. In a recent study, the frequency of CFTR mutation carriers was observed to be significantly higher in ABPA patients (6 of 21 patients; 28.5%) than in control asthmatic subjects (2 of 43 subjects;

4.6%; p=0.01) [Marchand et al, 2001]. Hence, susceptibility and resistance to ABPA may be associated with certain genetic factors.

Role of Human Lung Surfactant Proteins in Aspergillosis

Pulmonary surfactant proteins, SP-A and SP-D, are immune molecules which can directly interact with pathogens and allergens, stimulate immune cells and manipulate cytokine and chemokine profiles during host's immune response. Therapeutic administration of SP-A in murine model of invasive pulmonary aspergillosis can rescue mice from death. Treating mice, having ABPA, can suppress IgE levels, eosinophilia, pulmonary cellular infiltration and cause a marked shift from a pathogenic Th2 to a protective Th1 cytokine profile. These results highlight the potential of SP-A as novel therapeutics for lung allergy and infection. Therefore, the SP-A locus make particularly good candidate to be screened for predisposition to pulmonary infectious disease.

The human SP-A gene locus consists of 2 highly homologous functional genes, SP-A1 (GenBank Ref: M30838) and SP-A2 (GenBank Ref: M68519), and a pseudogene located on human chromosome 10q22.2-q23.1. Both functional genes consist of 4 coding exons. Karinch and Floros, 1995, reported that 5'UT of SP-A genes contains 4 (A, B, C, D for SP-A1) or 3 (A, B, D for SP-A2) untranslated exons, three of which (A, B, D) vary in length, and one of which C is new; these exons are alternatively spliced and the major splice patterns as well as their relative frequency vary between the two genes (the major pattern for SP-A1 is AD' [81%] and the major patterns for SP-A2 are ABD [44%] and ABD' [49%]). According to GenBank information there are six exons in SP-A2, including two non-coding and four coding exons (M68519). Several alleles that differ by a single amino acid had been identified in each SP-A gene (Floros et al., 1996). The alleles of the SP-A1 gene are denoted as '6A(n),' and those of the SP-A2 gene as '1A(n)' (Floros and Hoover, 1998). In Finland, Ramet et al. (2000) found that certain SP-A1 alleles, 6A(2) and 6A(3), and a SP-A1/SP-A2 haplotype, 6A(2)/1A(0), were associated with respiratory distress syndrome (RDS; 267450). The 6A(2) allele was overrepresented and the 6A(3) allele was underrepresented in infants with RDS. These associations were particularly strong among small premature infants born at gestational age less than 32 weeks. Ramet et al. (2001) reported that the frequency of specific surfactant protein-A haplotypes and genotypes differs between children with recurrent otitis media compared with a control population in Finland.

The prior art is lacking in any method that associates the allelic variants of SP-A2 gene to the ABPA susceptibility. The prior art is also lacking in any study that correlates the substructure of SP-A2 with predisposition to the ABPA.

Elevated levels of *A. fumigatus* specific IgE and IgG antibodies detectable by various serodiagnostic techniques is one of the important diagnostic criteria for ABPA. However, unfamiliarity with the diagnostic tests and nonavailability of certain serologic tests at clinical laboratories compounds the difficulty for the clinician. Reference standards of *Aspergillus* antigens for immunodiagnosis are not available till today either with the world health organisation (WHO) or any international agencies. This is mainly due to the complex nature of antigens of *Aspergillus* species, which require multiple purification processes. This is the first demonstration that relates to the application of SNP's in human SP-A2 gene for use such as molecular diagnosis and prediction of an individual's disease susceptibility to ABPA or otherwise, and/or the genetic analysis of SP-A2 gene in Indian population. The novelty of the present invention is in providing a method for detecting and associating allelic variants of SP-A2 gene with the disease for prediction of an individual's predisposition to ABPA.

OBJECTS OF THE INVENTION

The main object of the present invention is to provide method of detection of allelic variants of human SP-A2 gene useful for prediction of predisposition to aspergillosis.

Another object is to provide allele specific primers useful for detection of allelic variants of human SP-A2 gene.

Yet another object of the invention is to provide a method for establishing association of SP-A2 allelic variants with disease susceptibility.

Still another object of the invention is to provide a method for screening individuals carrying SP-A2 alleles predisposed to allergic bronchopulmonary aspergillosis.

SUMMARY OF THE INVENTION

The present invention relates to allelic variants of human SP-A2 gene and provides specific primers suitable for detecting these allelic variants for applications such as molecular diagnosis and prediction of an individual's disease susceptibility to ABPA or otherwise, and/or the genetic analysis of SP-A2 gene in Indian population. Two major *A. fumigatus* induced diseases are an allergic form, Allergic bronchopulmonary aspergillosis (ABPA) and an invasive form, Invasive pulmonary aspergillosis. Pulmonary aspergillosis is a serious threat to those immunocompromised as a result of disease or therapy, and has been identified as a major cause of morbidity and mortality in asthmatic and cystic fibrosis patients. Pulmonary surfactant protein, SP-A directly interacts with pathogens and allergens, stimulates immune cells and manipulates cytokine and chemokine profiles during host's immune response. Administration of SP-A to mice, having ABPA, can suppress IgE levels, eosinophilia, pulmonary cellular infiltration and cause a marked shift from a pathogenic Th2 to a protective Th1 cytokine profile. These results highlight the potential of SP-A as novel therapeutics for lung allergy and infection. The human SP-A gene locus consists of 2 highly homologous functional genes, SP-A1 (GenBank Ref: M30838) and SP-A2 (GenBank Ref: M68519), and a pseudogene located on human chromosome 10q22.2-q23.1. Both functional genes consist of 4 coding exons. Karinch and Floros, 1995, reported that 5'UT of SP-A genes contains 4 (A, B, C, D for SP-A1) or 3 (A, B, D for SP-A2) untranslated exons, three of which (A, B, D) vary in length, and one of which C is new; these exons are alternatively spliced and the major splice patterns as well as their relative frequency vary between the two genes (the major pattern for SP-A1 is AD' [81%] and the major patterns for SP-A2 are ABD [44%] and ABD' [49%]). According to GenBank information there are six exons in SP-A2, including two non-coding and four coding exons (M68519). Two polymorphisms at first base of $91^{st}$ codon (G/CCT, in exon 4, nucleotide position 1649 as per M68519) and third base of $94^{th}$ codon (AGA/G, in exon 4, nucleotide position 1660 as per M68519) were observed to be significantly associated with ABPA patients. The novelty of the present invention is in providing a method for detecting and associating allelic variants of SP-A2 gene with the disease for prediction of an individual's predisposition to ABPA.

DETAILED DESCRIPTION OF THE INVENTION

Figure 1:
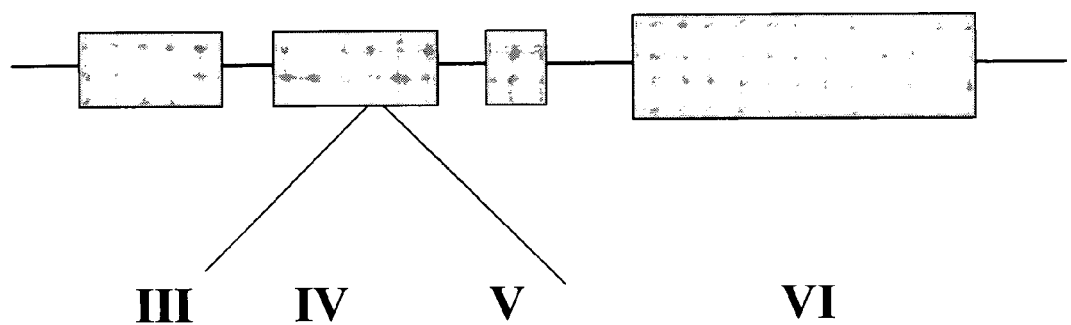
FIG. 1 is a schematic representation of the two SNP's in SP-A2 gene. The top line depicts the position of the four coding exons of the SP-A2 gene. The second line shows the relative locations of the two polymorphic sites. Both the polymorphisms are also shown in the sequence content of the gene.

The present invention relates to the detection of allelic variants of the human SP-A2 gene and their utility in predicting an individual susceptibility to the ABPA.

The region containing the SNP's was PCR amplified using the primers SP-A2 F (SEQ. ID No.4) and SP-A2 R (SEQ. ID No. 3). Approximately 100 ng of genomic DNA was amplified in a 50 .mu.l reaction volume containing a final concentration of 5 mM Tris, 25 mM KCl, 0.75 mM magnesium chloride (MgCl2), 0.05% gelatin, 20 pM of each primer and 1.5 U of Taq DNA polymerase. Samples were denatured at 95° C. for 5 min followed by 30 cycles of denaturation (95° C. for 1 min), annealing (70° C., 1 min), extension (72° C., 1 min) and a final extension of 7 min at 72° C. in a Perkin Elmer Gene Amp PCR System 9600. The PCR product was purified from band cut out of the agarose gel using QIA Quick gel extraction kit (QIAGEN) and was directly sequenced using dye terminator chemistry on an ABI Prism 377 automated DNA sequences with the PCR primers.

Accordingly, the present invention provides method for detection of human SP-A2 gene variants, useful for prediction of predisposition to aspergillosis, said method comprising the steps of:

(1) designing and synthesising specific oligonucleotide primers for PCR amplification of exon 4 of human SP-A2;

(2) amplifying genomic DNA of ABPA patients and normal control individuals using the above said primers;

(3) sequencing the amplified PCR product and identifying sequence variation computationally by comparing it with the already reported sequence of human SP-A2 gene (accession No. M68519);

(4) screening Normal Control individuals and ABPA patients for novel single nucleotide polymorphisms by sequencing amplified exon 4 of SP-A2 gene.

(5) computing the frequencies of G/C alleles (SNP at position 1649) and A/G alleles (SNP at position 1660) in normals and ABPA patients;

(6) establishing the association of G/C and A/G alleles with the ABPA disease based on their frequencies distribution on normal and ABPA patients; and (7) predicting the resistance or susceptibility to the ABPA based on the nucleotide present at the polymorphic sites in the individual tested, C allele (at nucleotide position 1649) and A allele (at nucleotide position 1660) being at low risk and G allele (at nucleotide position 1649) and G allele (at nucleotide position 1660) at high risk to the disease.

In an embodiment, the primers suitable for amplification of SP-A2 gene region containing the polymorphic sites 1649 and 1660, which may consist of SEQ ID No. 4, SEQ ID No. 3, & compliments thereof or any other pair of suitable primers.

In still another embodiment, allelic variants of SP-A2 gene have G/C and A/G haplotypes, Further, the invention provide a diagnostic kit for the detection of SNP haplotypes G/C or A/G comprising primers, suitable for amplification of SP-A2 gene region containing the polymorphic sites 1649 and 1660 and may consist of SEQ ID No. 4, SEQ ID No. 3, & compliments thereof or any other pair of suitable primers.

In another embodiment of the invention a nucleic acid vector may contain the allelic variants of SP-A2 gene.

In an embodiment of the invention, primers suitable for amplification of SP-A2 gene region containing one or more polymorphic sites are provided, said primers SEQ ID No. 4, SEQ ID No. 3, & compliments thereof or any other pair of suitable primers.

TABLE I

| Primers | S/ Location AS | Nt. position | Sequence |
|---|---|---|---|
| SEQ ID No. 3 (SP-A2 F) | Exon 4 S | 1602–1631 | 5' TGCCTCGTCCGCA TTCACCCTTCAGAC TGC 3' |
| SEQ ID No. 4 (SP-A2 R) | Intron 4 AS | 1980–2009 | 5' TGCCTGGAGCCCC TGGTGTCCCTGGAGAG C 3' |

S: Sense;
AS: Antisense;
Nt.: Nucleotide

Nucleotide positions in Table-I are according to SP-A2 gene sequence as in GenBank M68519.

The allelic variants of human SP-A2 gene may comprise one or more of the following SNP's as compared with the human SP-A2 gene sequence in the database (GenBank Acc NO. M68519).

TABLE-II

| Gene location | Nucleotides | | Amino acid | |
|---|---|---|---|---|
| | Position | Change | Position | Change |
| Exon 4 | 1649 | G/C | $91^{st}$ | Ala to Pro |
| Exon 4 | 1660 | A/G | $94^{th}$ | Arg to Arg |

The site of change is in accordance with the human SP-A2 gene sequence in the database (GenBank Acc No. M68519).

The invention also provides a method of analysing a nucleic acid from an individual for the presence of base at anyone of the polymorphic site shown in Table-II. This type of analysis can be performed on a plurality of individuals who are tested either for the presence or for predisposition to ABPA. The susceptibility to the disease can then be established based depending on the base or set of basis present at the polymorphic sites in the individuals tested.

Invention also provides oligonucleotide sequences (as listed in SEQ ID NO. 3-4, Table-I), suitable for use as allele specific primers for the detection of polymorphic sites listed in table-II.

Further, a diagnostic kit comprising one or more of the allele specific primers along with the required buffer and accessories suitable for identification of SP-A2 allelic variants to establish an individual's susceptibility to ABPA is also included in the invention.

Eukaryotic expression vectors comprising a DNA sequence coding for a protein or a peptide according to the invention are new materials and also included in the invention. Host cells, for example cloned human cell lines, can be transformed using the new expression vectors and are also included in the invention.

The manner in which the above-mentioned features, advantages and objects of the invention as well as others which will become clear are attained and can be understood in details by the particular description of the invention are illustrated in the appended drawings, however, that the appended drawings illustrate preferred embodiments of the invention and thereof not be considered limiting in their scope.

FIG. 1 is a schematic representation of the two SNP's in SP-A2 gene, wherein the top line depicts the position of the four coding exons of the SP-A2 gene, and the second line shows the relative locations of the two polymorphic sites. Both the polymorphisms are also shown in the sequence content of the gene.

Other and further aspects, features, and advantages of the present invention will be apparent from the following description of the preferred embodiments of the invention given for the purpose of disclosure. Alternative embodiments of the invention can be envisaged by those skilled in the art. All such alternative embodiments are intended to lie within the scope of this invention of this invention.

Polymorphisms of the Invention

As a first step to the present invention, the applicants carried out the PCR amplification of exon 4 of human SP-A2 gene (GenBank Acc. No. M68519). The sequencing of the purified PCR product revealed two SNP's in the exon 4 of human SP-A2 gene.

The present invention provides a sequence for the allelic variants of human SP-A2 gene comprising one or more of the following SNP's compared with the human SP-A2 gene sequence in the database.

TABLE-II

| Gene | Nucleotides | | Amino acid | |
|---|---|---|---|---|
| location | Position | Change | Position | Change |
| Exon 4 | 1649 | G/C | 91st | Ala to Pro |
| Exon 4 | 1660 | A/G | 94th | Arg to Arg |

The site of change is in accordance with the human SP-A2 gene sequence in the database (GenBank Acc No. M68519).

The first polymorphic site (A) as shown in FIG. 1, had either a G or a C. The second polymorphic site (B) contains either A or a G base. While the first substitution changes the amino acid sequence from Alanine to Proline, the second substitution is neutral. For example, the nucleotide sequence of the allelic variant of exon 4 of human SP-A2 gene having polymorphic sites as listed in table-II may be (SEQ ID NO:2)
5' gccccatggg tccacctgga gaaatgccat gtcctcctgg aaatgatggg ctgcctggag ccctggtat ccctggagag tgtggagaga aggggaggc tggcgagaga ggccctccag 3'.

In the above sequence the SNP's (A) and (B) are at nucleotide position 1649 and 1660 respectively and are shown in bold.

Association Analysis with the Disease

Analysis of these two SNP's in the 150 Normal and 40 ABPA patient chromosomes revealed that two haplotypes, possible with each SNP in a biallelic polymorphic system, were observed. The frequency in Normal and ABPA patient chromosome is summarised in Table-III.

TABLE III

| Poly-morph-ism | Allele percentages | | OR (95% CI) | Chi-square | |
|---|---|---|---|---|---|
| | ABPA | Controls | | Test | p-Value |
| 1649 G/C | n = 40 | n = 150 | | | |
| G | 34.09% | 19.56% | 2.1264 | | |
| C | 65.01% | 80.44% | 0.8152 < OR < 5.5468 | 2.426 | 0.1193 |
| 1660 A/G | | | | | |
| A | 75% | 93.48% | 4.7778 | 5.846 | 0.0156 |
| G | 25% | 6.52% | 1.2326 < OR < 18.5189 | | |

Further, studies on ABPA patient chromosomes revealed a high significant difference in the distribution of the two SNP's in the Normal and the ABPA patient chromosome (Table-III).

Figure 2:
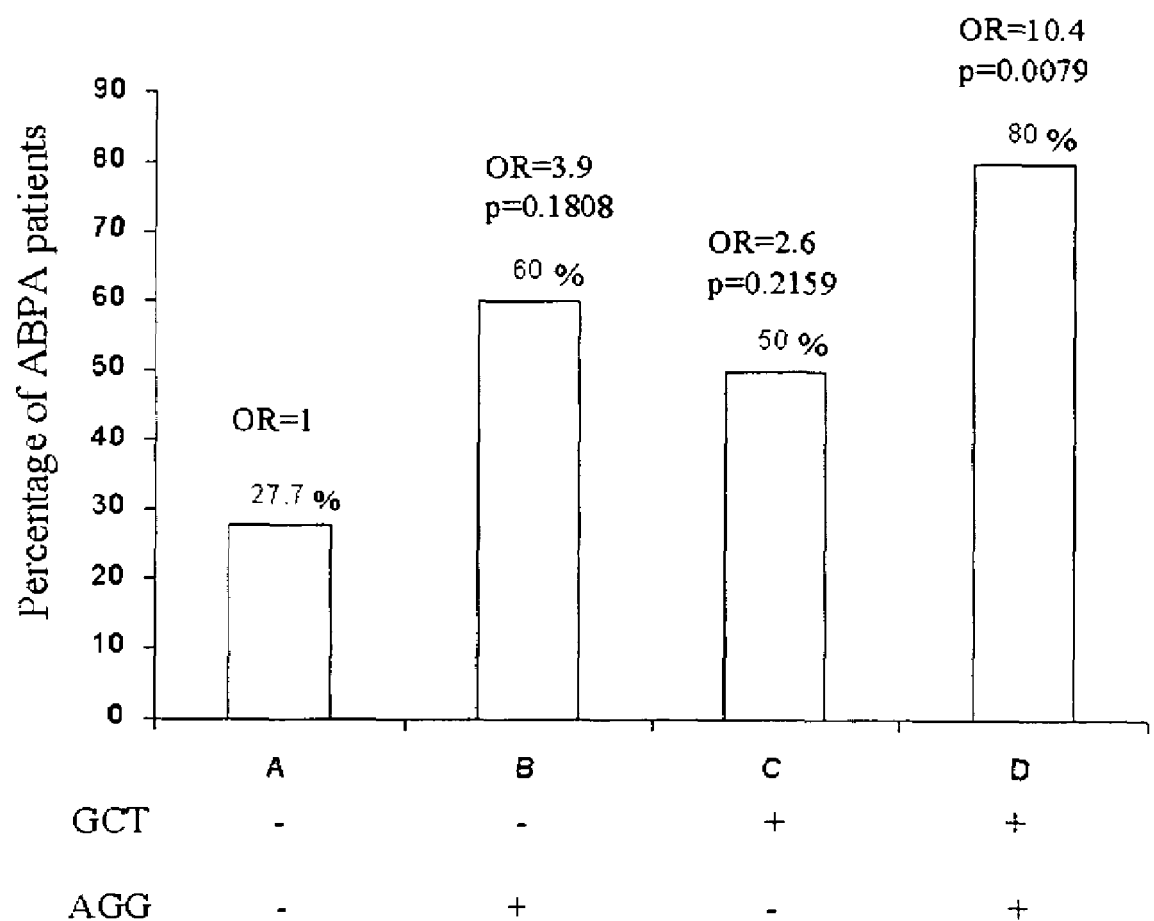
FIG. 2 is a graph illustrating the association between the co-occurrence of SP-A2 alleles GCT ($91^{st}$ codon) and AGG ($94^{th}$ codon) in allergic bronchopulmonary aspergillosis (ABPA) patients vs. controls. Values of OR and p (Cl 95%) are in comparison with the CCT/AGA genotype. "A" represents a group of ABPA patients carrying CCT and AGA alleles; "B" represents a group of ABPA patients carrying CCT and AGG alleles; "C" represents a group of ABPA patients carrying GCT and AGA alleles; and "D" represents a group of ABPA patients carrying GCT and AGG alleles.

Since, both the SNPs (1649 and 1660) are lying very close to each other, association of simultaneous occurrence of GCT and AGG alleles with ABPA was analysed. The co-occurrence of GCT and AGG alleles showed a stronger association with ABPA (FIG. 2). Eighty percent of the subjects carrying both the alleles are ABPA patients (p=0.0079; OR=10.4) whereas only 50% (C1649G) and 60% (A1660G) patients carry these two alleles separately. This is suggestive of an additive effect of these alleles of SP-A2 on disease outcome.

For each of the clinical markers of ABPA, GCT and AGG alleles were observed to be associated with severity (Table IV). Total IgE and eosinophilia were significantly higher in the group of ABPA patients carrying GCT and/or AGG alleles (IgE=19,625 IU/ml, % eosinophilia=18.1) in comparison to the patient group carrying CCT and AGA alleles (IgE=5,133 IU/ml, % eosinophilia=9.33; p=0.000 and 0.040 respectively). The % predicted $FEV_1$ in the group of ABPA patients carrying GCT and/or AGG alleles (56.0%) was lower than that for the group of ABPA patients carrying CCT and AGA alleles (68%). However, the difference between two patient populations was not statistically significant (p=0.150) with respect to $FEV_1$.

TABLE-IV

Clinical markers of ABPA severity split by SP-A2 91st and 94th codon polymorphisms

| | ABPA patients with genotype: 91st codon (GCT/NCT) and/or 94th codon (AGN) n = 18 Mean (S.D.) | ABPA patients with genotype: 91st codon (CCT) and 94th codon (AGA) n = 5 Mean (S.D.) | pValue (Student 't' test) |
|---|---|---|---|
| FEV$_1$ (%) | 56.0 (7.93) | 68 (12.2) | 0.150 |
| Total IgE (IU/ml) | 19,625 (14,500) | 5,133 (1,140) | 0.000 |
| Eosinophilia (%) | 18.1 (7.52) | 9.3 (5.79) | 0.040 |

S.D., Standard Deviation

Diagnostic Kit

The invention further provides diagnostic kit, comprising primers suitable for amplification of SP-A2 gene region containing one or more polymorphic sites are provided, said primers SEQ ID No.1, SEQ ID No.2, & compliments thereof or any other pair of suitable primers.

The invention further provides diagnostic kit, comprising primers suitable for amplification of SP-A2 gene region containing one or more polymorphic sites are provided, said primers SEQ ID No. 4, SEQ ID No. 3, & compliments thereof or any other pair of suitable primers.

EXPERIMENTAL

Example 1

Identification of Allelic Variants of SP-A2 Gene

This example describes the identification of allelic variant of human surfactant protein A2 gene by PCR and sequencing using certain oligonucleotide primers. According to the invention DNA was extracted from human peripheral blood leukocytes using a modification of salting out procedure. The concentration of the DNA was determined by measuring the optical density of the sample, at a wavelength of 260 nm. The DNA was then amplified by PCR by using the oligonucleotide primers:

The DNA was then amplified by PCR by using the oligonucleotide primers:

```
5' TGC CTG GAG CCC CTG GTG TCC CTG (SEQ. ID. No. 4)
GAG AGC 3' (Forward)

5' TGC CTC GTC CGC ATT CAC CCT TCA (SEQ. ID. No. 3)
GAC TGC 3' (Reverse).
```

The sample were denatured at 95° C. for 5 minutes followed by 28 cycles of denaturation (95° C., 1 minutes), annealing (70° C., 1 minute), extension (72° C., 1 minute) and a final extension of 7 minutes at 72° C. in a PE GeneAmp PCR System 9600. This reaction produced a DNA fragment of 459 bp when analysed by Genescan analysis by using ABI Prism 377 automated DNA sequencer. The PCR product was purified from band cut out of agarose gel using a Qiaquick gel extraction kit (Qiagen) and both the strands of the PCR product were directly sequenced using gel terminator chemistry on an ABI Prism 377 automated DNA sequencer with PCR prisms. The PCR products were shown to be identical to the human SP-A2 gene sequence in the database (acc. no. M68519), except for the previously mentioned 2 single base changes as listed in table II.

Example 2

Nucleotide Sequence of the Allelic Variant of SP-A2 Gene

The nucleotide seq. of the allelic variant of SP-A2 gene derived using the method as described in example 1.

In the above sequence the 2 SNP's as given in table II are at nucleotide position 1649 and 1660.

Example 3

Patients with A Allele at 1660 Position are at Nearly Zero Risk for the ABPA Disease A method as described in example 1 is applied to a series of DNA samples extracted from ABPA positive individuals and normal controls. There is observed a statistically significant difference (At position 1649 p=0.1193 and at position 1660 p=0.0156) in the frequency distributions of the SNP haplotypes generated using SNP in normal and ABPA patient SP-A2 chromosome. The results obtained are summarized in table below

TABLE-IV

| | SNP (G vs C) at 1649 position | SNP (G vs A) at 1660 position |
|---|---|---|
| ODDS RATIO (ABPA patient vs Normal) | 2.1264 | 4.7778 |
| Chi-square | 2.426 | 5.846 |
| p-value | 0.1193 | 0.0156 |

A strong association of G (at 1649 position) and G (at 1660 position) haplotypes with ABPA disease chromosome indicated that SP-A2 alleles with the G (at 1649 position) and G (at 1660 position) haplotypes are predisposed to the disease. Therefore, these SNP haplotypes in the human SP-A2 gene could be used as a method of establishing individual risk to ABPA. The association of G (at 1649 position) and G (at 1660 position) haplotypes with the ABPA disease was studied in Indian population. However, C (at 1649 position) and A (at 1660 position) haplotypes being at low risk and G (at 1649 position) and G (at 1660 position) haplotypes being at high risk for ABPA disease, can be expected to hold true for other human population also.

The invention shall be useful to establish genotype or base variation of SP-A2 gene. The information may be useful for molecular diagnosis, prediction of an individual's disease susceptibility to ABPA, prognosis and/or the genetic analysis of ABPA gene in a population. The frequency of these variants can also be used to predict the prevalence of ABPA disease among various populations.

Provided below is sequence listing information for SEQ ID Nos. 4 and 3, respectively.

Sequence Listing
General Information
APPLICANT: CSIR
TITLE OF INVESTIGATION: Method of detection of human SP-A2 gene variants
NUMBER OF SEQUENCES: 2
CORRESPONDENCE ADDRESS: Centre for Biochemical Technology
Tel 00-91-11-7666158 Fax.00-91-7667471

INFORMATION FOR SEQ ID No. 4
1 SEQUENCE CHARACTERISTICS:
LENGTH: 24 bp.
TYPE: DNA

5' TGC CTG GAG CCC CTG GTG TCC CTG GAG AGC 3'
ORGANISM: Artificial sequence
IMMEDIATE: Synthetic
NAME/KEY: Synthetic oligonucleotide
SEQUENCE ID #4
INFORMATION FOR SEQ ID No. 3
1 SEQUENCE CHARACTERISTICS:

LENGTH: 24 bp.
TYPE: DNA
5' TGC CTC GTC CGC ATT CAC CCT TCA GAC TGC 3'
ORGANISM: Artificial sequence
IMMEDIATE: Synthetic
NAME/KEY: Synthetic oligonucleotide
SEQUENCE ID #3

What is claimed is:

1. A method of detecting a predisposition to allergic bronchopulmonary aspergillosis, said method comprising steps of:
    (1) designing and synthesizing oligonucleotide primers capable of amplifying Exon 4 of human SP-A2 gene,
    (2) amplifying genomic DNA of allergic bronchopulmonary aspergillosis patients and normal control individuals using said primers of step (1),
    (3) sequencing the amplified genomic DNA and identify sequence variations of the amplified genomic DNA computationally by comparing it with an existing sequence of human SP-A2 gene,
    (4) screening normal control individuals and allergic bronchopulmonary aspergillosis patients for single nucleotide polymorphisms by sequencing of the amplified genomic DNA of the individuals using the said primers of step (1),
    (5) computing the frequency of G/C haplotypes at 1649 position and A/G haplotypes at 1660 position of allergic bronchopulmonary aspergillosis patients and normal control individuals,
    (6) establishing the association of G (at 1649 position) and G (at 1660 position) haplotypes with the allergic bronchopulmonary aspergillosis disease based on their frequency distribution in normal individuals and allergic bronchopulmonary aspergillosis patients, and
    (7) predicting the risk or susceptibility to allergic bronchopulmonary aspergillosis based on the haplotype present at the polymorphic sites in the individual tested, C (at 1649 position) and A (at 1660 position) haplotypes being at low risk and G (at 1649 position) and G (at 1660 position) haplotypes at high risk to the allergic bronchopulmonary aspergillosis.

2. A method as claimed in claim 1 wherein the oligonucelotide primers capable for amplification of said Exon 4 of said SP-A2 gene are selected from the group consisting of:
    (a) 5' TGC CTG GAG CCC CTG GTG TCC CTG GAG AGC 3' (SEQ. ID. No. 4), which is a forward primer, and
    (b) 5' TGC CTC GTC CGC ATT CAC CCT TCA GAC TGC 3' (SEQ. ID. No. 3). which is a reverse primer.

3. A method as claimed in claim 1 wherein the length of said oliognucleotide primers is between 5 and 100 bases.

4. A method as claimed in claim 1 wherein, the SP-A2 gene has allelic variants which have G/C and A/G halotypes.

* * * * *